(12) United States Patent
Chen

(10) Patent No.: US 11,061,019 B2
(45) Date of Patent: Jul. 13, 2021

(54) HIGH SENSITIVITY OPTICAL DETECTION SYSTEM

(71) Applicant: Jinghong Chen, Milpitas, CA (US)

(72) Inventor: Jinghong Chen, Milpitas, CA (US)

(73) Assignee: Jinghong Chen, Milpitas, CA (US)

( * ) Notice: Subject to any disclaimer, the term of this patent is extended or adjusted under 35 U.S.C. 154(b) by 0 days.

(21) Appl. No.: 16/009,187

(22) PCT Filed: Jun. 14, 2018

(86) PCT No.: PCT/US2018/037590
§ 371 (c)(1),
(2) Date: Jun. 14, 2018

(87) PCT Pub. No.: WO2019/240801
PCT Pub. Date: Dec. 19, 2019

(65) Prior Publication Data
US 2020/0264167 A1    Aug. 20, 2020

Related U.S. Application Data

(60) Provisional application No. 62/519,181, filed on Jun. 14, 2017, provisional application No. 62/549,401, filed on Aug. 23, 2017.

(51) Int. Cl.
*G01N 33/52* (2006.01)
*G01J 3/10* (2006.01)
(Continued)

(52) U.S. Cl.
CPC .............. *G01N 33/52* (2013.01); *G01J 3/10* (2013.01); *G01J 3/28* (2013.01); *G01N 21/31* (2013.01);
(Continued)

(58) Field of Classification Search
CPC .... G01N 33/52; G01N 21/31; G01N 21/6486; G01N 2201/0221; G01N 21/33;
(Continued)

(56) References Cited

U.S. PATENT DOCUMENTS 4,962,986 A * 10/1990 Hompel ............... G02B 6/2852
250/227.11
5,496,700 A * 3/1996 Ligler ................... G01N 33/569
435/4
(Continued)

*Primary Examiner* — Mohamed K Amara

(57) ABSTRACT

A high sensitivity optical system for detection of chemical and biological analytes is disclosed comprising a vessel containing the chemical and biological analytes, a light-guide inside the vessel but separated from the vessel by the chemical and biological analytes, one or more excitation light sources at one end of the vessel, a detector at another end of the vessel, one or more excitation filters between the excitation light sources and the vessel, one or more emission filters between the vessel and the detector, and light directing components. The novel optical system is secured in a housing and connected to devices extrinsically or intrinsically for data input, process, display, storage, and communication. This optical system could enable clinical level diagnosis of a wide range of diseases in an inexpensive mobile point-of-care format. Furthermore, the form factor of the optical system can be significantly reduced to form a highly integrated lab-on-a-chip system.

18 Claims, 5 Drawing Sheets

(51) Int. Cl.
  *G01J 3/28* (2006.01)
  *G01N 21/31* (2006.01)
  *G01N 21/64* (2006.01)

(52) U.S. Cl.
  CPC .... *G01N 21/6486* (2013.01); *G01J 2003/102* (2013.01); *G01N 2201/0221* (2013.01)

(58) Field of Classification Search
  CPC ......... G01N 21/645; G01N 2201/0806; G01N 21/35; G01J 3/10; G01J 3/28; G01J 2003/102; G01J 3/4406; G01J 3/0272
  See application file for complete search history.

(56) References Cited

U.S. PATENT DOCUMENTS

| | | | | |
|---|---|---|---|---|
| 5,763,277 | A * | 6/1998 | Zhu | G01N 21/645 204/452 |
| 5,809,185 | A * | 9/1998 | Mitchell | G01N 21/648 250/227.11 |
| 7,314,751 | B2 * | 1/2008 | Kelleher | G01N 21/6428 385/12 |
| 7,385,460 | B1 * | 6/2008 | Wang | H01P 5/00 333/108 |
| 7,479,404 | B2 * | 1/2009 | Cunningham | B82Y 20/00 438/32 |
| 7,521,769 | B2 * | 4/2009 | Cunningham | G01N 21/00 257/414 |
| 7,737,392 | B2 * | 6/2010 | Cunningham | G01N 21/4133 250/214.1 |
| 8,889,424 | B2 * | 11/2014 | Ehrenkranz | G01N 33/78 436/164 |
| 8,947,656 | B2 * | 2/2015 | Cunningham | G01N 21/658 356/300 |
| 9,366,814 | B2 * | 6/2016 | Gray | G01N 21/6452 |
| 9,658,152 | B2 * | 5/2017 | Zimmerle | G01J 3/50 |
| 10,072,308 | B2 * | 9/2018 | Lee | C12Q 1/701 |
| 10,571,395 | B2 * | 2/2020 | Karlovac | H04N 7/18 |
| 2003/0058440 | A1 * | 3/2003 | Scott | G01N 21/6428 356/318 |
| 2003/0059853 | A1 * | 3/2003 | Lockhart | G01N 21/7703 435/7.9 |
| 2004/0022475 | A1 * | 2/2004 | Pennington | G02B 6/1221 385/12 |
| 2004/0209354 | A1 * | 10/2004 | Mathies | B01L 3/50273 435/287.2 |
| 2005/0070005 | A1 * | 3/2005 | Keller | C12N 15/1037 506/4 |
| 2005/0153320 | A1 * | 7/2005 | Herron | C12Q 1/683 435/6.11 |
| 2006/0098927 | A1 * | 5/2006 | Schmidt | G01N 21/59 385/129 |
| 2006/0139634 | A1 * | 6/2006 | Scott | G01J 3/10 356/318 |
| 2006/0202133 | A1 * | 9/2006 | Ok | G01J 3/10 250/458.1 |
| 2006/0206010 | A1 * | 9/2006 | Iida | G16H 50/80 600/300 |
| 2006/0222567 | A1 * | 10/2006 | Kloepfer | G01N 33/558 422/68.1 |
| 2006/0279732 | A1 * | 12/2006 | Wang | G01J 3/02 356/326 |
| 2007/0077595 | A1 * | 4/2007 | Koo | G01J 3/0218 435/7.1 |
| 2008/0268548 | A1 * | 10/2008 | Zuckerman | G01N 21/658 436/172 |
| 2009/0202193 | A1 * | 8/2009 | Foerster | G02B 1/046 385/12 |
| 2010/0105035 | A1 * | 4/2010 | Hashsham | G01N 21/645 435/6.19 |
| 2010/0173394 | A1 * | 7/2010 | Colston, Jr. | B01F 13/0062 435/287.2 |
| 2010/0187106 | A1 * | 7/2010 | Sadik | G01N 33/5302 204/403.01 |
| 2010/0202726 | A1 * | 8/2010 | Egalon | G01N 21/64 385/12 |
| 2011/0130652 | A1 * | 6/2011 | Boppart | A61B 3/102 600/425 |
| 2011/0280863 | A1 * | 11/2011 | Buhimschi | G01N 33/53 424/130.1 |
| 2012/0157160 | A1 * | 6/2012 | Ozcan | B01L 3/502715 455/556.1 |
| 2013/0071850 | A1 * | 3/2013 | Duer | G01N 21/6452 435/6.12 |
| 2014/0193839 | A1 * | 7/2014 | Cunningham | G01J 3/0264 435/7.92 |
| 2014/0211204 | A1 * | 7/2014 | Stedtfeld | C12Q 1/686 356/244 |
| 2015/0247806 | A1 * | 9/2015 | Cohen | G01N 21/76 436/172 |
| 2015/0268244 | A1 * | 9/2015 | Cho | G01N 15/1463 435/7.23 |
| 2016/0022745 | A1 * | 1/2016 | Wang | A61P 31/04 424/93.3 |
| 2016/0024552 | A1 * | 1/2016 | Reardon | C12Y 114/13 435/25 |
| 2016/0054343 | A1 * | 2/2016 | Holmes | G01N 21/75 506/2 |
| 2016/0060697 | A1 * | 3/2016 | Devaux | C12Q 1/6883 514/44 A |
| 2017/0059563 | A1 * | 3/2017 | Smith | G01N 21/6454 |
| 2017/0167984 | A1 * | 6/2017 | Bosse | G01N 21/64 |
| 2019/0194728 | A1 * | 6/2019 | Brandon | C12Q 1/689 |

* cited by examiner

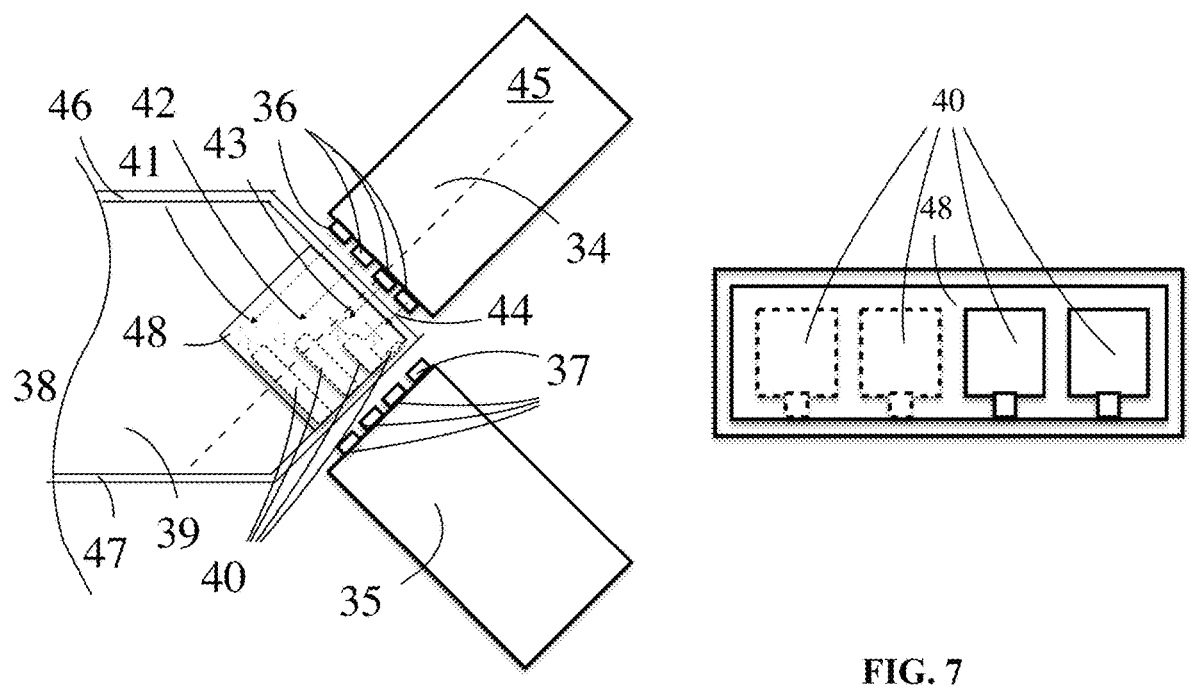
FIG. 6
FIG. 7
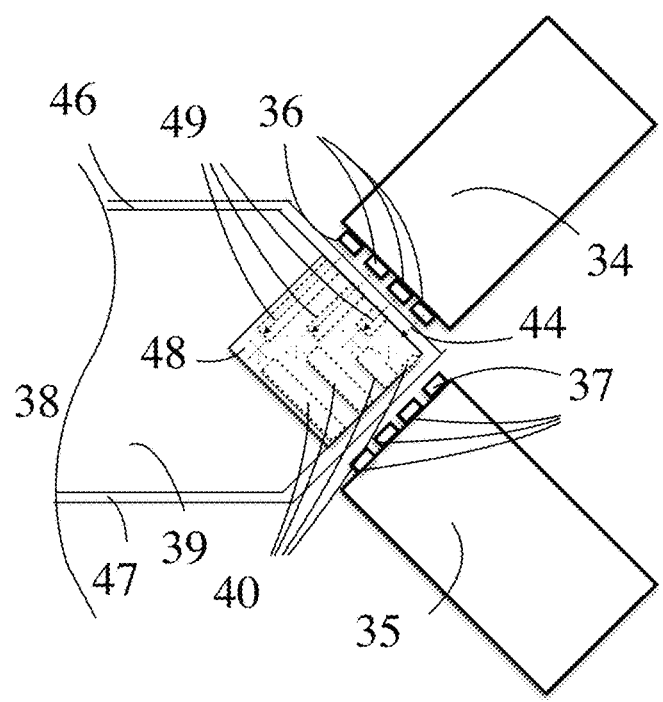
FIG. 8

HIGH SENSITIVITY OPTICAL DETECTION SYSTEM

FIELD OF THE DISCLOSURE

The present application relates to optical systems for detection of chemicals and biological analytes, and more specifically to mobile optical detection systems for point-of-care (POC) applications that deliver high sensitivity from small volumes and very low concentration samples yet using small and low cost optical components.

BACKGROUND

Point of care (POC) testing has steadily increased in recent years largely driven by delivering less costly preventative care closer to the patient's home in the developed world and more effective care for infectious diseases in the developing world. However, until today the dominant success has been the glucose biosensor, lateral flow strips as cardiac markers, and pregnancy test.

Wide spread of POC technologies is limited by the testing ability from small handheld devices and the high cost of bench-top devices which are essentially laboratory instruments reduced in size and complexity. The key to broader POC adoption remains to be how to transfer the sophisticated disease testing capability and sensitivity of microscopy and spectroscopy from the laboratory to small mobile devices with low cost components and without the associated inferior performance. The ever increasing use of mobile phones worldwide and rapid rate of mobile technology development have raised the hope and triggered unprecedented research of mobile devices to be utilized for medical diagnostics in recent years. POC devices can reduce cost by taking advantage of the extrinsic and intrinsic sensors, and ubiquitous accessibility of communication, computation, display, and data storage. However, the various intrinsic sensors selected solely for mass consumer applications are yet to find commercial success in providing enhancement of detection sensitivity.

Fluorescent labeling is widely used for biochemical analysis and disease diagnosis. The standard devices for fluorescent detection are fluorometer, fluorescence spectroscopy, and enzyme-linked immunosorbent assay (ELISA) plate-reader used in high through-put bioassays to detect the presence of a substance. In the above mentioned instrumentations, both fluorescence excitation and emission are greatly attenuated in the liquid solution before reaching to the detector. As a result, the light collection efficiency is low, often requiring high power and expensive photomultiplier tube (PMT) to amplify the weak signals.

Various approaches have been investigated to increase the sensitivity, including multiplication of the diagnostic targets such as culture or polymerase chain reaction (PCR), use of high selectivity and high intensity molecular labeling probe, use of high sensitivity optical detection systems, etc. This invention focus on improving sensitivity of optical detection systems.

SUMMARY

The present invention provides design principles of a high sensitivity optical detection system that include a vessel containing the chemical and biological analytes, a light-guide inside the vessel but separated from the vessel by the chemical and biological analytes, one or more excitation light sources) at one end of the vessel, a detector at another end of the vessel, one or more excitation filters between the excitation light sources and the vessel, one or more emission filters between the vessel and the detector, and other optical components to direct light. The optical system can be used to detect emissive or absorptive materials in the volume between the vessel and the light-guide, and/or on their surfaces. This optical system can achieve large signal and signal to noise (S/N) ratio for quantitative analysis even with low cost and small form factors components. The high sensitivity comes from the effective light excitation of the materials, the highly efficient emission guided to the detector by the light-guide and/or the vessel side wall, and noise isolation between the light source(s) and the detector(s). This novel optical system and its variants enable clinical level diagnosis in an inexpensive mobile point of care (POC) format which could be a key to trigger broader POC adoption for wide range of disease detections.

In the preferred embodiment, the optical system has an end LED and two side LEDs, a glass light-guide and vessel, a fluorescence analyte solution, a pair of filters, a photodiode detector, and lens in the emission and detection optical paths. The optical system is hosted in opaque mechanical structure(s) which eliminate noise from the ambient light, prevent light leakage from the excitation light source(s), and only allow light through the designated optical path. It is linked externally with phone, tablet, or computer etc for data input, process, display, storage, and communication. The optical system can generate a detection signal and sensitivity similar to commercial fluorometer and enzyme-linked immunosorbent assay (ELISA) plate reader.

In one embodiment, instead of being a stand alone unit with single or an array of the above optical structures, the optical system can also be combined with other detection systems such as a mobile microscope to form a qualitative and quantitative detection apparatus.

Another embodiment and its variants, for example, may be implemented in the existing analytical instrumentations such as ELISA plate reader. A fixture attached with repeating light-guides can be placed inside the wells of ELISA plate to achieve higher sensitivity.

Another embodiment and its variants, for example, can be incorporated in existing micro-fluidic devices such as GeneXpert to further improve the detection sensitivity by insertion of excitation light-guides and/or emission light-guides.

Another embodiment and its variants, for example, can be used as a lab-on-a-chip system, which is composed of highly integrated light source(s), micro-fluidic analyte chambers, analytes, light detectors, waveguide structures inside micro-fluidic analyte chambers, filters, patterned lens and other micro optical components. When associated optical components are tunable in a wide range of spectrum, the device can function as various spectroscopies such as fluorescence, UV-Vis, and IR spectroscopy, etc.

While multiple embodiments are disclosed, still other embodiments of the present invention will become apparent to those skilled in the art from the following Detailed Description. As will be realized, the embodiments are capable of modifications in various aspects, all without departing from the spirit and scope of the embodiments. Accordingly, the drawings and detailed description are to be regarded as illustrative in nature and not restrictive.

BRIEF DESCRIPTION OF THE DRAWINGS

The present invention is further detailed with respect to the following drawings. These figures are not intended to limit the scope of the present invention but rather illustrate certain attributes thereof.

FIG. 6 is a 2D view of a modification to micro fluidic chip in GeneXpert, adding emission light-guides in the fluidic chamber to improve detection sensitivity.

FIG. 7 is a 2D view of the cross section of the emission light-guides inside GeneXpert micro fluidic chamber in FIG. 6. The bottom of the light-guide attachment to the bottom wall of the micro fluidic chamber could be continuous, or with small posts to reduce optical leakage through the wall.

FIG. 8 is a 2D view of another modification to GeneXpert micro fluidic chip, adding excitation and emission light-guides in the fluidic chamber to further improve detection sensitivity.

DETAILED DESCRIPTION

In the following description of examples, reference is made to the accompanying drawings which form a part hereof, and in which it is shown by way of illustrating specific examples that can be practiced. It is to be understood that other examples can be used and structural changes can be made without departing from the scope of the disclosed examples.

The present invention provides a low cost mobile apparatus for high sensitivity optical detection of chemical and biological analytes, more specifically a POC device for wide range of disease diagnosis. The novel optical device configuration is designed to maximize the excitation, efficiently collect and guide the fluorescence signal to a detector, increasing signal-to-noise ratio by translating excitation noise into signal, and isolate noise of the light source from the detector.

Figure 1:
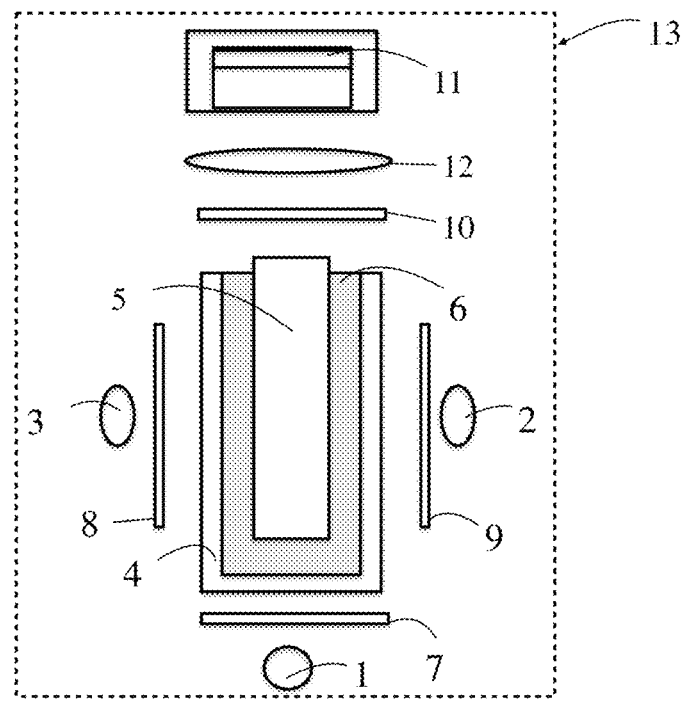
FIG. 1 illustrates a 2D view of an exemplary high sensitivity optical detection system and associated optical components according to the preferred embodiment.

FIG. 1 shows a 2D view of the high sensitivity optical detection system 13. This system 13 includes a vessel 4, a light-guide 5 inside the vessel, excitation light source 1 at one end of the vessel, and/or excitation light source 2-3 on the side of the vessel, a photodetector 11 at another end of the vessel, excitation filters 7-9 and emission filter 10 after excitation light source(s) 1-3 and before photodetector 11 respectively. The optical system 13 is used to detect analyte 6 in liquid phase or solid phase format in the volume between the vessel 4 and the light-guide 5 and/or on their surfaces. Lens 12 and/or other optical components are optional between light source(s) 1-3 and vessel 4, and/or between light-guide 5/vessel 4 and photodetector 11 if needed. This optical system 13 can achieve large signal and high sensitivity for quantitative analysis even with low cost LED light source(s) 1-3 and silicon photo detector 11.

The light source 1-3 can be Mercury or Xenon arc lamps, laser, light emitting diode (LED), and organic light emitting diode (OLED); there can be one or more end light source 1 and side light source 2-3, the end and side light source could be used alone or in various of combinations. Vessel 4 and light-guide 5 can be made of materials such as glass, quartz, other inorganic materials, polymeric materials, or metal; Vessel 4 and light-guide 5 can be transparent, or partially opaque, or partially covered by opaque materials; Vessel 4 and light-guide 5 can be cylindrical, a rectangular or other shapes; light-guide 5 can be solid or hollow, or other structures; the height of the light-guide 5 can be the same as the vessel 4 wall or different. Filters 7-10 can be absorption filters, interference filters, and diffraction filters. Detector 11 can be photodiode, CMOS, CCD, or PMT. Lens 12 could be a single lens or a compound lens made of glass or polymeric materials. Analyte 6 can be solution or dispersion of biological species such as sputum, urine, blood etc. which can be treated or as is. Analyte 6 can be self absorptive or emissive, or tagged with absorptive or emissive materials.

Figure 2:
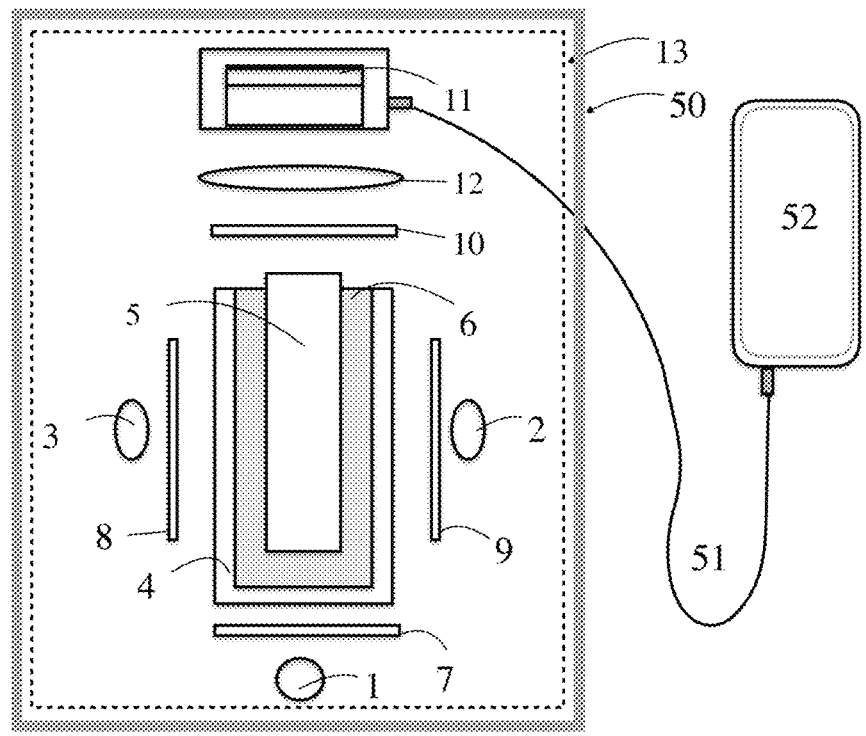
FIG. 2 is a 2D view of an exemplary high sensitivity optical detection system in mechanical enclosure and connected to mobile phone according to the preferred embodiment.

FIG. 2 illustrates an optical apparatus with element 13 hosted in a small opaque mobile enclosure 50 that would allow ease of insertion and removal of the test vessel 4 and the light-guide 5. The mobile enclosure 50 eliminates noise from the ambient light and block light leakage from the excitation light source(s), only allows light through the designated optical path and in selected areas.

FIG. 2 also shown that the above optical apparatus can be linked externally via connector 51 with mobile phone, tablet, or computer 52 etc. for data input, process, display, storage, and communication. The optical system 13 can also be used as an attachment to the intrinsic sensors of mobile device such as camera, ambient light sensor (ALS), proximity sensor. In this case, the photodetector 11 is replaced by camera CMOS, ambient light sensor (ALS), proximity sensor. The high sensitive optical detection system 13 narrows the gap between the sophisticated disease testing capability and sensitivity of spectroscopy in the laboratory and small mobile devices with low cost components, could be a key to trigger broader POC adoption for many disease detection, including massive epidemics such as HIV, Tuberculosis, etc., chronic illness of diabetes, heart and vascular risks, hormone imbalance, and many more. It can also be utilized for food safety inspection.

Figure 3:
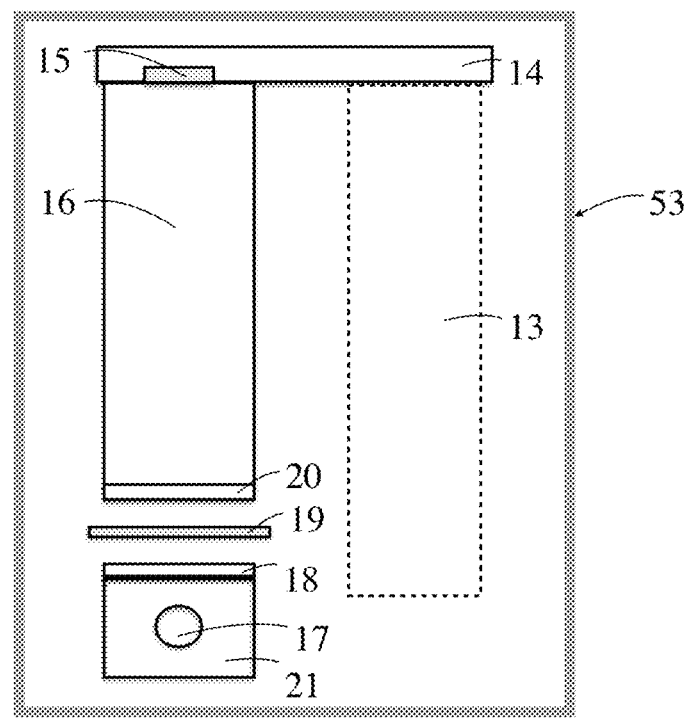
FIG. 3 is a 2D view of an exemplary mobile apparatus with the optical system in FIG. 1 and microscope attached to phone camera.

The optical 13 and its variants can be used in combination with other detection systems such as a mobile microscope to form a mobile diagnosis apparatus, which is preferably used in certain setting if an optical image is also desirable. FIG. 3 shows a 2D view of a mobile apparatus with the optical system 13 in FIG. 1 and microscope 16 attached to the camera 15 of the mobile phone 14. Light source 17 is placed in a small enclose 21. An excitation filter 18 is placed on top of the enclosure 21, above which is the test sample 19. An emission filter 20 is attached to the end of the microscope 16. The entire setup can be placed in a mechanical housing 53 to eliminate noise from the ambient.

Figure 4:
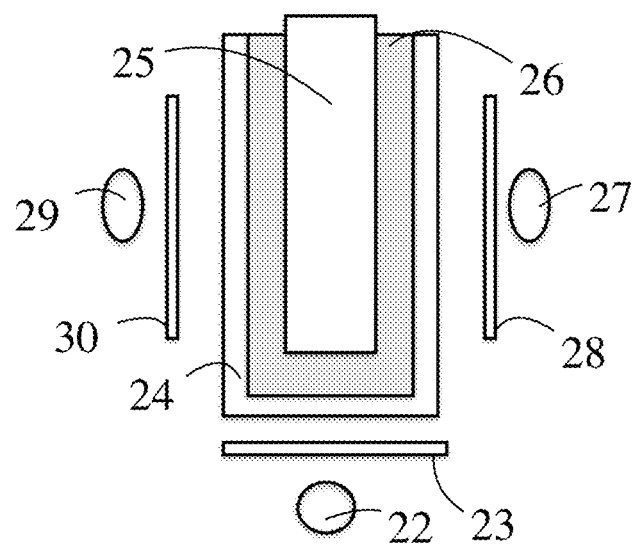
FIG. 4 is a 2D view of an exemplary ELISA plate with light-guide and side light sources for better signal sensitivity.
Figure 5:
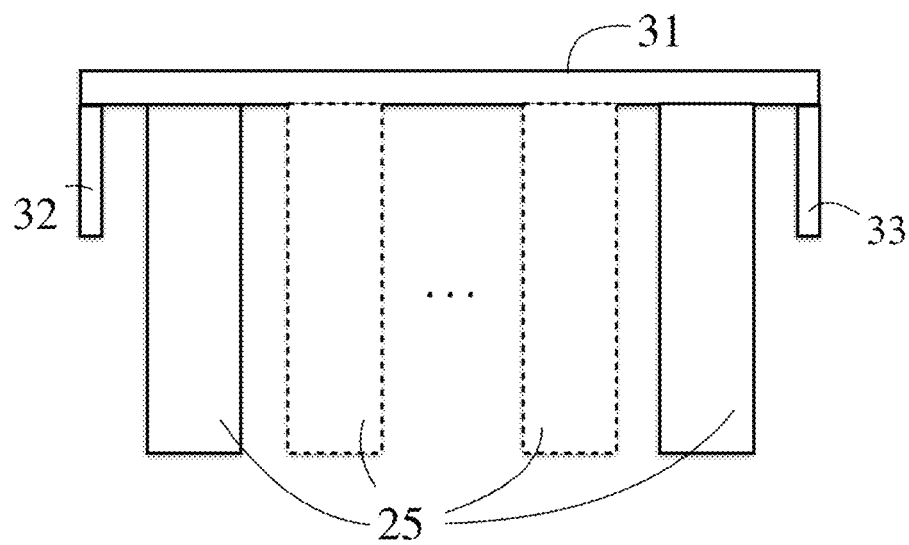
FIG. 5 is a 2D view of an exemplary fixture with light-guide(s) and end features to attach to ELISA plate.

The optical system 13 and its variants can also be implemented as a component in the existing apparatus such as ELISA plate reader. FIG. 4 shows a 2D view of the ELISA plate 24 with light-guide 25 and side light sources 27 and 29 for better signal sensitivity. Light source 22 and filter 23 represent the original light source and filter in ELISA plate reader. Light source 27, 29 and filter 28, 30 represent the additional light sources and filters for improved detection sensitivity. 26 is the analyte in the form of solution or dispersion of biological species such as sputum, urine, blood etc. which can be treated or as is. FIG. 5 shows a 2D view of an exemplary fixture 31 with light-guide 25 and end features 32-33 to attach to ELISA plate(s) 24. A fixture 31 molded with repeated light-guides 25 can be placed inside current ELISA plate (s) 24 to achieve higher sensitivity. Features 32-33 at the two end of the fixture 31 are used to control the insert depth of the light-guides 25 and secure fixture 31 on ELISA plate (s) 24. The ELISA surface treatment can be either on the micro-plate or on the wave-guiding fixture or on both. If the ELISA surface treatment is on the micro-plate, the wave-guiding fixture could be reusable.

The optical system 13 and its variants can also be implemented in micro fluidic chip design to further improve the detection sensitivity. FIG. 6 shows a 2D top view of GeneXpert micro fluidic chip 39 of on the side of the cartridge 38. 46 and 47 represent microfluidic inlet and outlet respectively. 48 is the fluidic chamber where PCR amplified materials are being excited and their fluorescence is detected from the side at 90 degree angle. 36 are the excitation light sources in light box 34, and 37 are the emission light detectors in detector box 35. 41-44 are the excitation light path. Emission light-guides 40 are added to the fluidic chamber 48 to improve detection sensitivity.

FIG. 7 shows a 2D view of the cross section of the emission light guides 40 inside GeneXpert micro fluidic chamber 48 along the cross section line 45 in FIG. 6. The bottom of the light-guide attachment 40 to the bottom wall of the micro fluidic chamber 48 could be continuous or use two or more small posts to reduce optical leakage through the wall.

In another configuration, FIG. 8 shows a 2D view of GeneXpert micro fluidic chip 39 of on the side of the cartridge 38. All are the same as FIG. 6 except excitation light-guides 49 are added to the fluidic chamber to further improve detection sensitivity.

Figure 9:
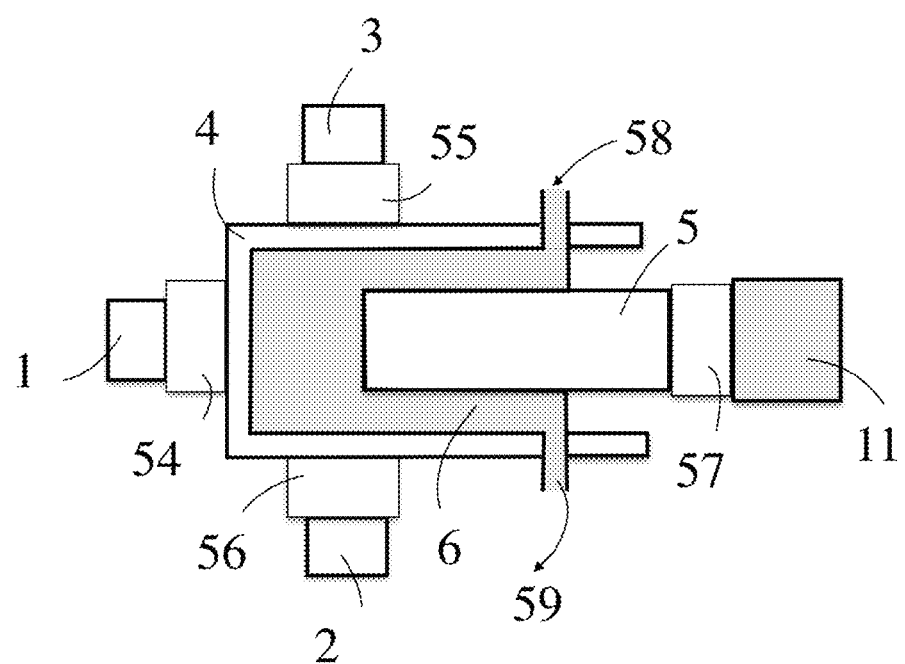
FIG. 9 illustrates a 2D view of an exemplary lab-on-a-chip system, which is composed of an integrated light source, micro-fluidic analyte chambers, analytes, a light detector, waveguide structures inside the micro-fluidic analyte chambers, filters, patterned lens and other micro optical components.

FIG. 9 illustrates a 2D view of an exemplary lab-on-a-chip system, which is composed of integrated light source, micro-fluidic analyte chambers, analytes, light detector, waveguide structures inside the micro-fluidic analyte chambers, filters, patterned lens and other micro optical components. The optical system of the lab-on-a-chip solution could be in single or array format. When associated optical components are tunable in a wide range of spectrum, the device can function as various spectroscopies such as fluorescence, UV-Vis, and IR spectroscopy, etc. As the degree of integration increases and the size of each components shrinks, less amount of analyte samples is required for each test.

The foregoing description is illustrative of particular embodiments of the invention, but is not meant to be a limitation upon the practice thereof. The following claims, including all equivalents thereof, are intended to define the scope of the invention.

What is claimed is:

1. An optical system for detection of chemical and biological analytes comprising a vessel containing the chemical and biological analytes, a light-guide inside the vessel but separated from the vessel by the chemical and biological analytes, a plurality of absorption and excitation light sources at one end of the vessel, a detector at another end of the vessel, a plurality of filters between the plurality of absorption and excitation light sources and the vessel, a plurality of filters between the vessel and the detector, lenses, mirrors, gratings, and polarizers along a plurality of absorption, excitation and emission optical paths, wherein said absorption and excitation light sources are disposed longitudinally and transversally with respect to a major axis of the light-guide enabling thereby absorption light and excitation light to couple into the light-guide after they pass through the chemical and biological analytes.

2. The optical system of claim 1, wherein the said plurality of absorption and excitation light sources:
   comprise Mercury or Xenon arc lamps, lasers, LEDs, or OLEDs; and
   are pointed to and aligned with a light-guide center axis, or orthogonal to the light-guide center axis around a vessel sidewall.

3. The optical system of claim 1, wherein the said light-guide or vessel:
   is made of glass, quartz, other inorganic materials, polymeric materials, metals, or a combination thereof;
   is transparent, partially opaque, or partially covered by opaque materials;
   is cylindrical, cuboid, triangular prism, other polygonal prism, or a combination of thereof; and
   is solid or hollow, in full or partial.

4. The optical system of claim 1, wherein the said chemical and biological analytes:
   are absorptive or emissive materials, between the vessel and the light-guide, and/or on their surfaces; and
   are self-absorptive, self-emissive, or tagged with absorptive or emissive materials.

5. The optical system of claim 1, wherein the said plurality of filters:
   are absorption filters, interference filters, diffraction filters, or a combination of thereof; and
   are in a single, or an array format.

6. The optical system of claim 1, wherein the said detector comprises one or more photodiodes, CMOS detectors, CCDs, PMTs, cameras, video cameras, or webcams.

7. The optical system of claim 1, wherein the said optical system is composed of discrete, partially integrated, or highly integrated optical components in a single, an array, or a plurality format.

8. The optical system of claim 1, wherein the said optical system:
   is connected extrinsically via a connector or wireless communication to a device, such as a mobile or stationary phone, a tablet, a computer, a watch, or other devices with data input, process, display, storage, and communication capabilities; or
   is attached to an intrinsic optical sensor of the device, such as a camera sensor, an ambient light sensor (ALS), or a proximity sensor inside the mobile or stationary phone for data input.

9. The optical system of claim 8, wherein the said optical system and the device are essential low-cost, mobile point-of-care set-ups for quantitative detection of very low concentration of the chemicals and biological analytes, or are used in combination with other detection systems such as a mobile microscope to form an optical detection apparatus with rapid visual imaging and quantitative measurement of a concentration of the chemical and biological analytes.

10. The optical system of claim 9, wherein the said mobile microscope is a stand alone unit connected to a common structure of the said optical detection apparatus, or is attached to an intrinsic optical sensor of the device, such as a camera sensor inside the mobile or stationary phone.

11. The optical system of claim 9, wherein the said optical detection apparatus is secured in a mechanical housing, isolated from ambient noise and protected from mechanical impact.

12. The optical system of claim 1, wherein the said optical system is implemented in existing instrumentations such as enzyme-linked immunosorbent assay (ELISA) plate-reader by adding a plurality of light-guides to a multi-well plate to further improve detection sensitivity.

13. The optical system of claim 1, wherein the said optical system is implemented in micro fluidic based instrumentations such as GeneXpert by adding the one or more excitation and/or emission light-guides in a fluidic analyte chamber to further improve detection sensitivity.

14. The optical system of claim 1, wherein the said optical system is a lab-on-a-chip system:
   wherein the vessel is one or more micro-fluidic analyte chambers; and
   the lab-on-a-chip system comprises additional light detectors, one or more waveguide structures inside the one or more micro-fluidic analyte chambers;
   is in discrete, partially integrated, or highly integrated format;
   is in a single, an array, or a plurality format;
   is functioning as various spectrometers for fluorescence, luminescence, UV-Vis, or IR spectroscopy, tunable in a wide range of spectrum; and
   is assembled on a substrate of silicon, glass, ceramics, metals, polymers, or a combination thereof.

15. An apparatus for detection of chemical and biological analytes comprising:
   an optical system composed of a vessel containing the chemical and biological analytes, a light-guide inside the vessel but separated from the vessel by the chemical and biological analytes, a plurality of absorption and excitation light sources at one end of the vessel, a detector at another end of the vessel, a plurality of filters between the plurality of absorption and excitation light sources and the vessel, a plurality of filters between the vessel and the detector, lenses, mirrors, gratings, and polarizers along a plurality of absorption, excitation and emission optical paths, wherein said absorption and excitation light sources are disposed longitudinally and transversally with respect to a major axis of the light-guide enabling thereby absorption light and excitation light to couple into the light-guide after they pass through the chemical and biological analytes;
   a housing to which the optical system is secured; and
   a device with data input, process, display, storage, and communication capabilities.

16. The apparatus of claim 15, wherein the said housing:
   is made of metals, alloys, ceramics, polymeric materials, or a combination thereof;
   is rigid, semi-rigid, or flexible;
   is in a geometry to confine a location and exposure area of the one or more excitation light sources, to allow ease of insertion and removal of the vessel and the light-guide, and to block noise of the one or more excitation light sources from reaching the detector;
   is opaque such that the said optical system is isolated from ambient noise; or
   is semi-transparent or transparent, but covered with one or more opaque coatings.

17. The apparatus of claim 15, wherein the said device:
   is a mobile or stationary phone, a tablet, a computer, a watch, or other devices with data input, process, display, storage, and communication capabilities;
   is linked extrinsically via a connector or wireless communication to the said optical system; or
   is attached directly to the said optical system via an intrinsic sensor of the said device, such as a camera sensor, a video camera sensor, an ambient light sensor (ALS), or a proximity sensor inside a mobile or stationary phone.

18. The apparatus of claim 15, wherein the said apparatus is in a single, an array, or a plurality format.

* * * * *